United States Patent [19]

Allan

[11] Patent Number: 5,574,227
[45] Date of Patent: Nov. 12, 1996

[54] PAPER BOARD CREASE FORCE MEASURING DEVICE

[75] Inventor: Russell J. Allan, Alphington, Australia

[73] Assignee: Amcor Limited, South Melbourne, Australia

[21] Appl. No.: 507,321

[22] PCT Filed: Mar. 23, 1994

[86] PCT No.: PCT/AU94/00142

§ 371 Date: Aug. 22, 1995

§ 102(e) Date: Aug. 22, 1995

[87] PCT Pub. No.: WO94/22010

PCT Pub. Date: Sep. 29, 1994

[30] Foreign Application Priority Data

Mar. 23, 1993 [AU] Australia .................................. PL7950

[51] Int. Cl.$^6$ ........................................................ G01N 3/20
[52] U.S. Cl. ........................................................ 73/849; 73/854
[58] Field of Search ............................ 73/849, 852, 854, 73/760

[56] References Cited

U.S. PATENT DOCUMENTS

| | | |
|---|---|---|
| 2,044,411 | 6/1936 | Vaughan, Jr. . |
| 2,338,338 | 1/1944 | Kieckhefer .................. 73/854 |
| 2,637,996 | 5/1953 | McKee et al. . |
| 2,646,679 | 7/1953 | Buker ............................ 73/854 |
| 2,885,661 | 5/1959 | Brown et al. ................. 73/854 |
| 2,934,945 | 5/1960 | Geenen et al. ............... 73/854 |
| 3,099,153 | 7/1963 | Rutledge . |
| 3,548,650 | 12/1970 | Boadle . |
| 3,868,849 | 4/1975 | Hunyar ......................... 73/854 |
| 4,179,941 | 12/1979 | Walter . |
| 4,358,962 | 11/1982 | Ashby et al. . |
| 5,178,017 | 1/1993 | Dinzburg . |
| 5,419,202 | 5/1995 | Howard et al. .............. 73/849 |

FOREIGN PATENT DOCUMENTS

| | | |
|---|---|---|
| 2745182 | 4/1979 | Germany . |
| 1191286 | 5/1970 | United Kingdom . |
| 2231670 | 11/1990 | United Kingdom . |

OTHER PUBLICATIONS

Patent Abstract of Japan, "Bending Tester", P-1084, May 11, 1990, 2-124443 (A), Yasuki Ikeda(2).

*Primary Examiner*—Richard Chilcot
*Assistant Examiner*—Max H. Noori
*Attorney, Agent, or Firm*—Bell, Seltzer, Park & Gibson, P.A.

[57] ABSTRACT

An apparatus and method for determining the crease characteristics of a corrugated paper board sample including a sample location area, a load cell located such that a portion of the surface of the sample overlies the load cell, and a creasing edge which abuts a portion of the sample on the surface opposite the surface which overlies the load cell. Thus the portion of the sample opposite the load cell can be manually lifted to crease the product about the creasing edge, causing the portion of the sample which overlies the load cell to bear against the load cell, and with the force being measured by the load cell.

6 Claims, 4 Drawing Sheets

PAPER BOARD CREASE FORCE MEASURING DEVICE

This invention relates to an apparatus and method for measuring the creasing characteristics of paper board.

In high speed box making machines and automated packing lines it is important that the consistency and quality of creases is closely controlled and maintained. If this is not done successfully the potential to form false creases in paper board which can cause the jamming of machines or the production of malformed boxes is increased.

Thus it is important to be able to assess the variation in creasing characteristics in different types of paper board. The characteristics of interest include the peak force required to fold the board, the ratio of forces required to fold creased and uncreased board and the force required to fold the board at a predetermined angle.

The measurement of the peak force required to fold the paper board is useful in assisting the box maker to assess the quality of the board and therefore the parameters under which box production can occur with minimal jamming and production of malformed boxes.

The determination of the peak force generated at a specified angle during the folding of paper board can also be useful to know for specific operations. Some packing machines only fold the crease through a small angle —less than the angle at which the maximum force will occur. If this smaller force proves to be a significant fraction of the force required for uncreased board there is the possibility that an uncreased part of the board will fold rather than the crease itself, leading to deformation of the box and runnability problems. Alternatively, if the force at the required angle is much less than the uncreased paper board creasing force then there will be no problem—independent of whether the peak force is close to the uncreased board creasing force or not.

The ratio of forces required to fold creased and uncreased board provides a useful assessment of the potential to form false creases. In order to determine the quality of creases in a board sample, a Score Bend Test has been used for quantifying "crease quality". It involves the measurement of the force required to fold a creased line and the measurement of the force required to fold an uncreased line parallel to the crease. Usually, the crease quality is expressed as a % Score Ratio or a foldability coefficient which is calculated as the ratio of the peak folding force of the creased board to the peak folding force of the uncreased board.

As the measurement of peak folding force, peak force at an angle and the calculation of the % Score Ratio to determine the crease quality of board is important in the manufacture of boxes and board products there have been numerous attempts to develop a machine which measures crease quality and other characteristics of both corrugated boards and carton boards quickly and easily.

In one conventional instrument for measuring these forces, the specimen is placed across the top of a "Y-shaped" support and a pressure bar is situated above the support. The Y-shaped support moves upwards controlled by a motor such that the test specimen is forced against the pressure bar which is connected to a mechanical force gauge. The pressure bar must be positioned either over the score line of a creased sample or over the flute tip of the corrugations of an uncreased sample. Such machines are cumbersome and time consuming to use because the sample must be positioned on the support and aligned very carefully. Misalignment of the sample will lead to an inaccurate result. These machines are also fairly complicated because they require a motor to move the Y-shaped support. They are also bulky which is not desirable in manufacturing plants, due to the requirement that the apparatus be combined with a motor.

Additionally there have been other types of apparatus proposed which measure the flexural resistance of board products. The flexural resistance measurements provide an indication of the boards tendency to buckle under load which is an important characteristic to consider when the board is to be used in industrial packaging operations. U.S. Pat. No. 5,106,477 describes an apparatus for measuring the flexural resistance of ribbed cardboard, for example, corrugated board. The patent discloses an apparatus wherein an uncreased corrugated board sample is clamped between two supports, the two supports and the uncreased sample are then moved by a motor upwards such that the uncreased sample comes into contact with a roller connected to a load cell. As the uncreased sample connects with the roller, it is bent and the force required to bend the uncreased sample is recorded by the load cell. The apparatus disclosed in the U.S. patent is only designed to measure the flexural resistance of an uncreased sample. This machine however, is also complicated and time consuming to use. It too requires careful placement of the sample between two clamps which must then be suitably tightened. The machine requires a motor to move the sample into contact with the roller which is bulky and increases the likelihood of problems with operation of the machine.

Because of these difficulties the proposed apparatus have not been widely used for measuring crease quality and other characteristics of board products. The most commonly used measure of crease quality is for an experienced box-maker to wave a sample in his hand and observe the ease of forming a fold line.

It is an object of this invention to overcome at least some of these disadvantages of the prior art by providing a simple apparatus for measuring the crease quality and other characteristics of paper board which is quick and easy to use.

The invention therefore provides an apparatus for determining the crease characteristics of a corrugated paper board sample including a sample location area;

a load cell located such that a portion of the surface of the sample abuts the load cell; and a creasing edge which abuts a portion of the sample on a surface opposite to the surface which abuts the load cell.

In general, it is preferred that the portion of the sample on the side of the creasing edge remote from the load cell is adapted for rotation toward the load cell and it is also preferred that the creasing edge about which the sample is bent remains stationary with respect to the load cell during measurement. Thus, it is particularly preferred that the force measured by the load cell is exerted on the load cell in the same rotational direction as the force exerted on the sample.

It is also preferred that the sample is bent about the creasing edge manually and is therefore not mechanically or electrically driven.

Furthermore, the invention also provides a method for determining the crease characteristics of a corrugated paper board sample including loading the sample in a sample location area;

bending the sample about a creasing edge such that the portion of the sample on the side of the creasing edge remote from the load cell is rotated towards the load cell; and measuring the force required to bend the sample with the load cell.

It is preferred that during the determination of the force required to bend the sample around the creasing edge, the creasing edge remains stationary with respect to the load cell. It is also preferred that the sample is folded about the creasing edge manually.

The load cell is any device capable of measuring an applied force within a suitable range i.e. from 0 to 50 newton. The load cell may be located above, below or to the side of the portion of the board sample abutting it.

The creasing edge may take the form of a bar or a wedge, however, as those skilled in the art would aware it can also take the form of equivalents such as a piece of wire or lugs located at either edge of a sample to commence the crease. Depending on the location of the load cell relative to the sample, the creasing edge may form part of the sample location area.

Thus the invention advantageously provides an apparatus and a method for the determination of crease characteristics of a sample of paper board quickly and easily. The apparatus is easy to operate allowing for the rapid repetition of tests. When manually operated, the apparatus is compact, portable and has minimal power requirements.

The invention is, in part, predicated on the discovery that the maximum force required to fold a crease is independent of the rate at which the crease is folded. It is therefore preferable that there be no form of control over the rate at which the board is bent. It is not necessary to use a motor to provide a constant and consistent rate for the folding of a sample, thus resulting in lower running costs and a more compact design. In contrast to all prior art instruments for measuring crease related properties the sample is bent over the crease edge in the same direction as the force measured by the load cell.

A preferred embodiment of this invention will now be described with reference to the following figures.

Figure 1:
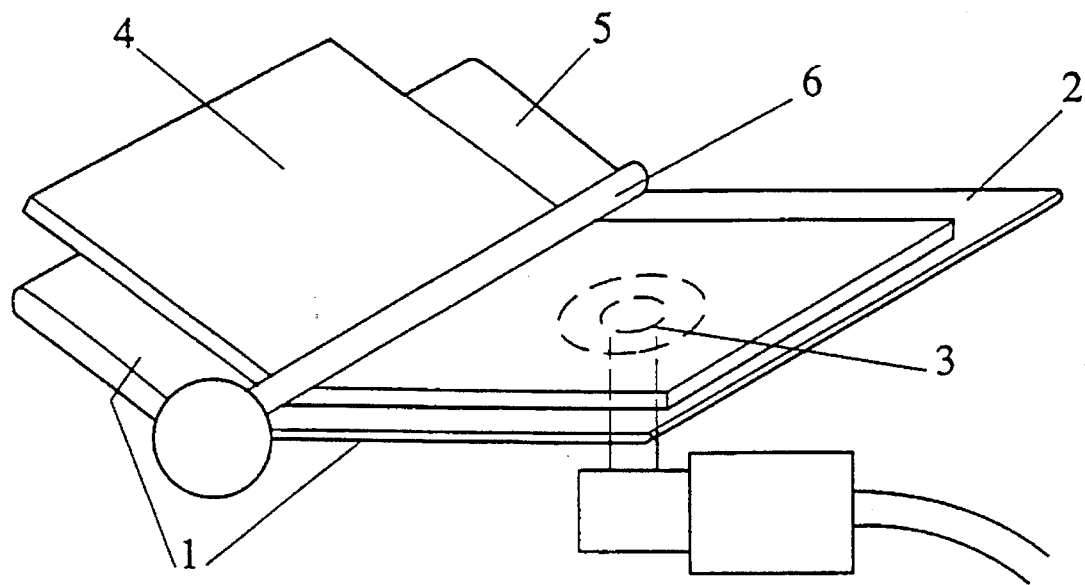
FIG. 1 shows a schematic view of the apparatus according to the invention.
Figure 3:
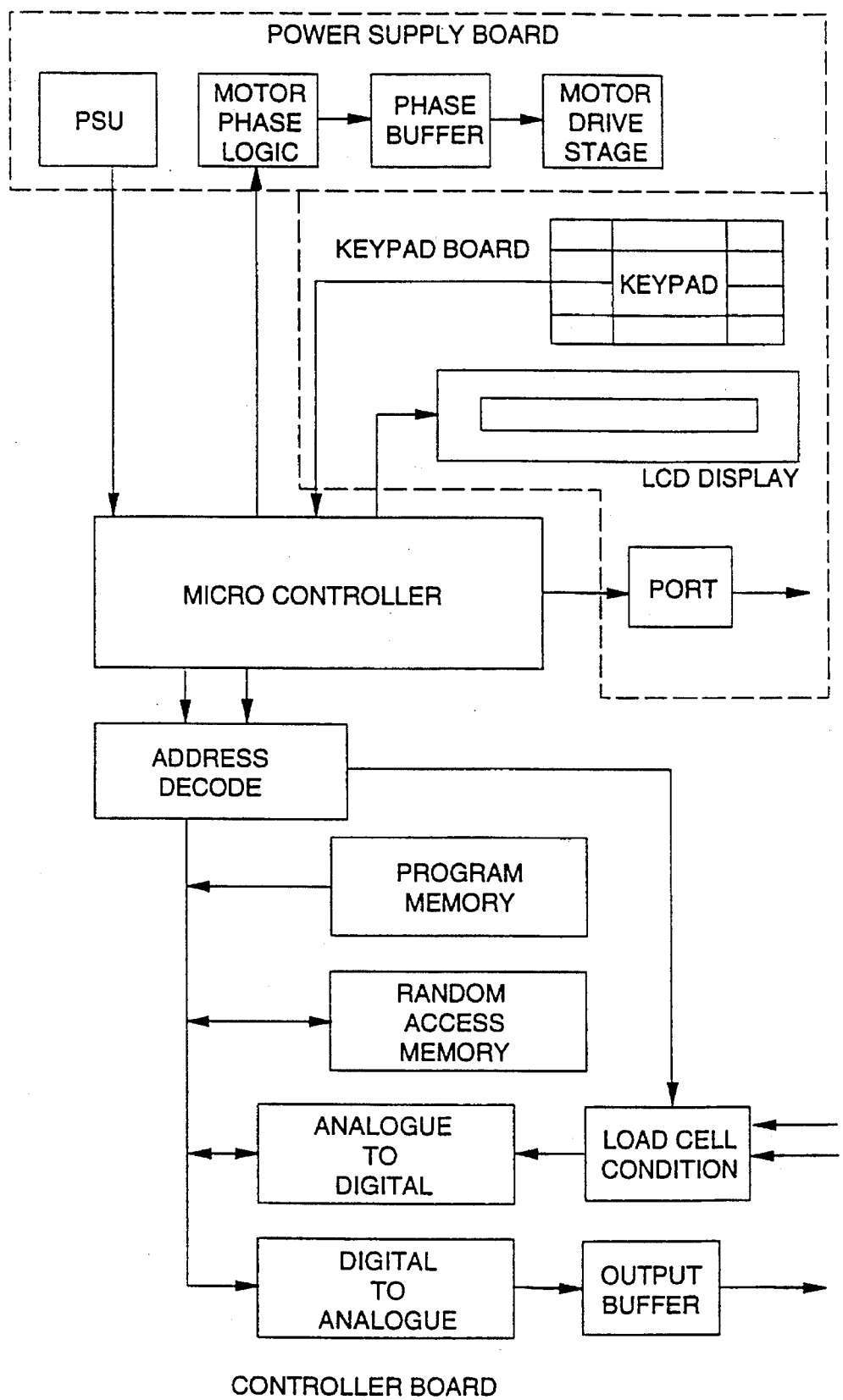
FIG. 3 shows a functional flow chart for the apparatus according to the invention.

The apparatus comprises a paper board sample location area (1) which consists of an arm (5) and a load cell table (2). The load cell (3) is located under the load cell table (2) so that the force exerted by the paper board sample (4) (shown in FIG. 1 only) on the load cell table (2) can be measured by the load cell (3). The apparatus also comprises a creasing edge (6) about which the sample is folded during testing. The load cell is connected to a computer or microprocessor which is capable of taking numerous measurements, recording, storing and analysing the results. The apparatus may be connected to a printer to enable the information obtained to be printed. FIG. 3 shows the force folding tester functional flow chart—(PSU refers to power supply unit). The operation of the tester may be divided into four sections: sample identification, serial output, option menu and calibration.

The apparatus can be used to perform the following tests:

PEAK FORCE TEST

To maintain maximum efficiency on high speed box making machines and automated packing lines, the quality of creases must be controlled. The apparatus subject of this invention provides a quick, easy and repeatable assessment of crease quality.

Figure 2:
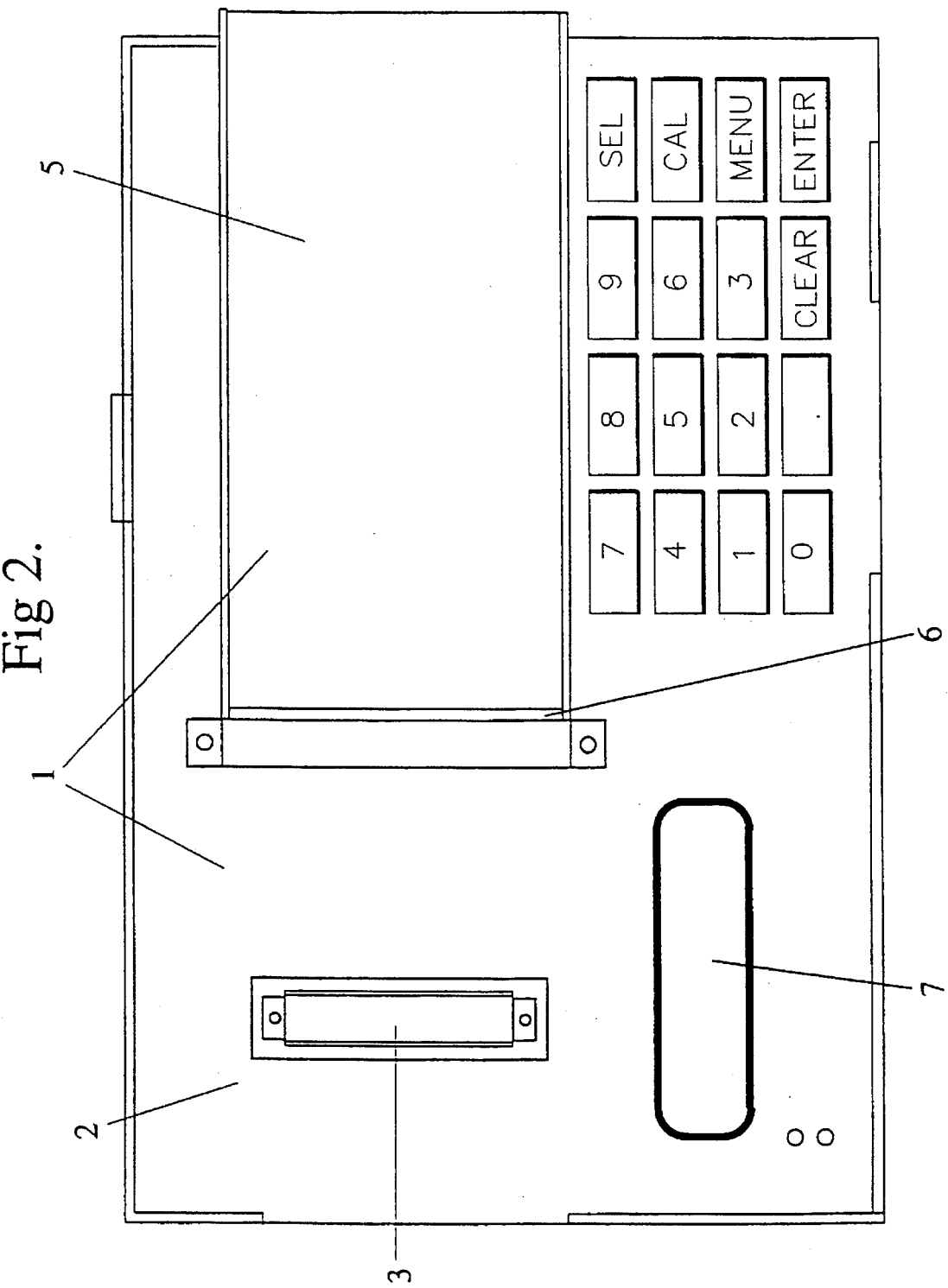
FIG. 2 shows a diagram of the apparatus according to the invention.

The folding force tester shown in FIG. 2 allows for the manual folding of both creased and uncreased corrugated paper board. The fold may be made in both the cross direction ie., parallel to the flutes or in the machine direction ie., at right angles to the flutes. The test folds the board about 90° from the planar position. The peak force generated by the test sample (not shown) during the folding action is measured by the load cell (3) and is displayed on the display of the tester (7). The preferred load cell is an XTRAN 100N load cell which is obtained from Applied Measurement.

To carry out the test a template is required for cutting 100 mm wide strips of paper board. The sample should be at least 100 mm wide so that the crease position (either previously creased or not) lies squarely across the 100 mm width. The sample should be at least 150mm long, and preferably 200 mm long, cut so as to provide a distance between one end of the sample and the crease position of 120 mm.

It is important to avoid unnecessary stressing of the crease position before testing. Designate and record the position of the crease position in the box blank or sheet on the sample with a felt tip pen to avoid damaging it. It is possible that creases in various positions on a box blank may be designed purposely to give different folding force results. The level of folding force results will also depend upon the paper board grade being tested.

Prepare at least four equivalent test pieces for the nominated crease position. These should be taken from identical box blanks at the same position in the blank. Then calibrate the folding force tester if necessary.

Place the 120 mm length of the sample on the sample location area (1) such that the crease position is located directly below the creasing edge (6). Generally, the sample should be placed so that the inside liner of the box is facing upwards during testing. However, for some packaging machine operations it may be necessary to test with the inside liner facing down.

Place a hand under the lip of the arm (5) and smoothly lift the arm through an arc until the movement is arrested by a hinge stop (not shown). Immediately return the arm to the horizontal position. As the arm is returned to the horizontal position the peak folding force will be displayed on the display (7) and will continue to be displayed until the next sample is tested. The angle at which the peak force occurs is also displayed.

Repeat this test for all samples. As the series of tests progresses, the last test value, the mean value and the standard deviation of the test series and N, the number of tests are shown on the tester display (7). The peak force is measured in newtons and the apparatus in general can measure between 0 and 30 newtons. The resolution of the measurements is in the order of 0.01 newton.

THE SCORE TEST RATIO

The score test ratio reports the ratio of the maximum force generated by the folding of creased board to that when folding uncreased board. This is used to allow box makers to take into account the variation between different types of boards when measuring crease resistance to folding. This test provides for the quantifying of the degree of creasing or the damage incurred by the board during the creasing process.

The score test ratio is defined as follows:

$$\text{SCORE TEST RATIO } (\%) = \frac{\text{Peak folding force of the crease} \times 100}{\text{Peak folding force of the uncreased board}}.$$

Prepare the samples as described above (Peak Force Test) but preparing at least four equivalent pairs (creased/uncreased) of samples for the nominated crease position. These should be taken from identical box blanks as close as possible to the same position in the blank. It is important to avoid unnecessary stressing of the crease before testing. Calibrate the apparatus if necessary.

In response to the display (7) flashing TEST THE CREASED BOARD, place the 120 mm length of the creased sample on the sample location area (1) such that the crease is positioned directly below the creasing edge (6). Generally, the sample should be placed so that the inside liner of the box is facing upwards during testing. However, for some packaging machine operations it may be necessary to test with the inside liner facing down.

Place a hand under the lip of the arm (5) and smoothly lift the arm through an arc until the movement is arrested by a hinge stop (not shown). Immediately return the arm to the horizontal position. As the arm is returned to the horizontal position the display will ask for the uncreased board sample for testing.

Insert the uncreased board sample, ensuring that the orientation of the uncreased sample is identical to the corresponding creased sample. Repeat the procedure for all the creased and uncreased sample pairs. As the series of tests progresses, the last test ratio, the mean value and standard deviation of the test series and N, the number of tests are shown on the tester display.

Figure 4:
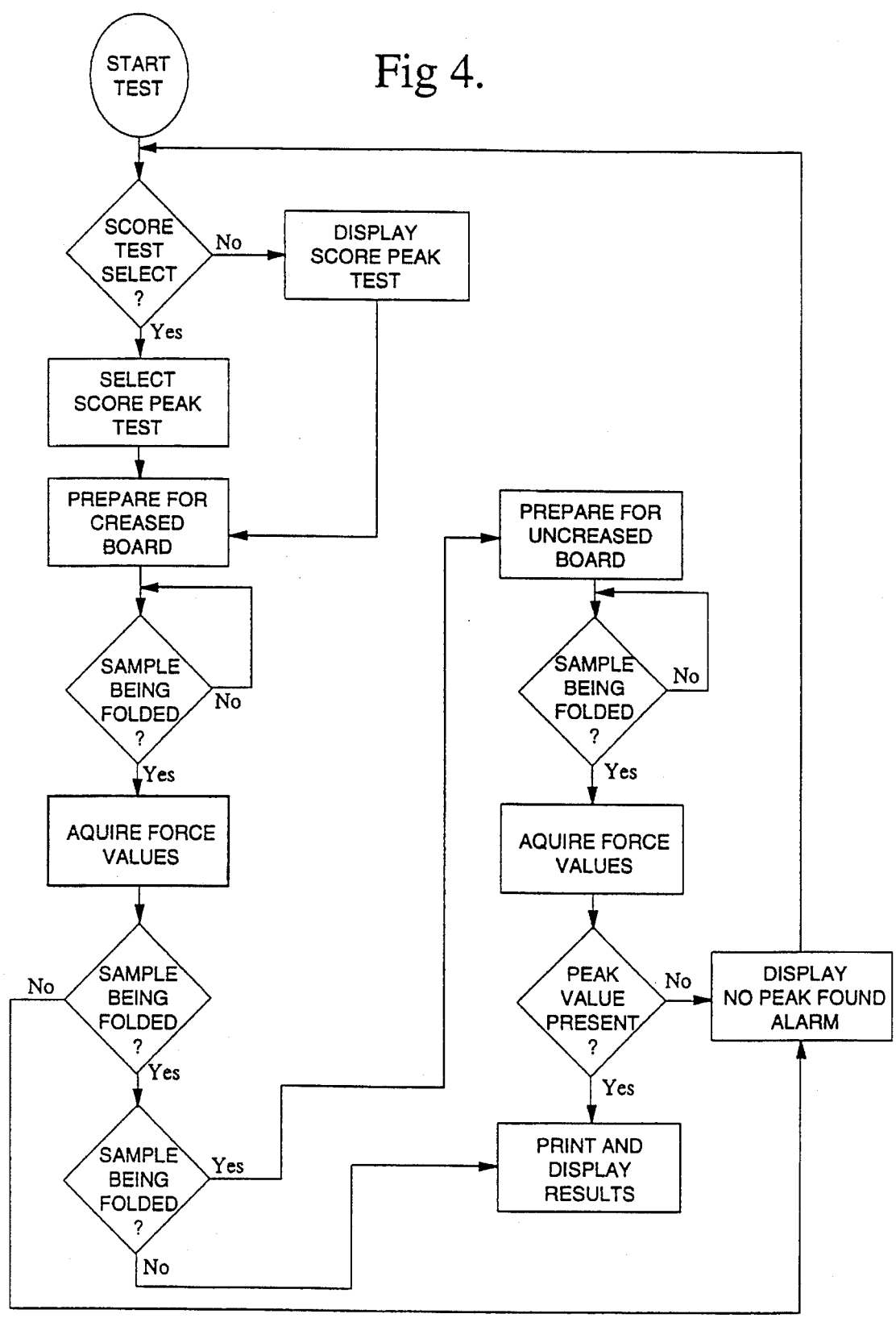
FIG. 4 shows a test function flow chart for the apparatus according to the invention.

FIG. 4 shows the test function flowchart for determining the peak force or the score ratio.

PEAK FORCE AT ANGLE

The determination of the peak force at a specified angle can be done by selecting the "at angle" test. This can be useful if a particular angle is meaningful in a specific operation. When selecting this test, the operator is prompted to enter the angle at which the force is to be measured. The apparatus has a sensor located at the point of rotation of the sample which records the angle and correlates this to the force recorded by the load cell.

Prepare the samples as described above (Peak Force Test). These should be taken from identical box blanks as close as possible to the same position in the blank. It is important to avoid unnecessary stressing of the crease before testing. Calibrate the apparatus if necessary.

Place the 120 mm length of the sample on the sample location area (1) such that the crease is positioned directly below the creasing edge (6). Generally, the sample should be placed so that the inside liner of the box is facing upwards during testing. However, for some packaging machine operations it may be necessary to test with the inside liner facing down.

Place a hand under the lip of the arm (5) and smoothly lift the arm through an arc until the movement is arrested by a hinge stop (not shown). Immediately return the arm to the horizontal position. The result is reported on the display, indicating the force at a particular angle as well as the mean and standard deviation for the series of tests. If desired, the output can be graphed on a FORCE vs ANGLE plot which may be useful when the shape of the force plot is required for analysis.

The claims defining the invention are as follows:

1. An apparatus for determining the crease characteristics of a corrugated paper board sample, said apparatus comprising:

a sample location area;

a load cell for measuring an applied force, said load cell being located within said sample location area such that one surface of a sample positioned on the sample location area overlies the load cell; and a creasing edge positioned to transversely overlie the sample location area at a location laterally spaced from the load cell, wherein the creasing edge is adapted to transversely overlie the opposite surface of a sample positioned on the sample location area, and wherein a portion of the sample on the side of the creasing edge remote from the load cell can be rotated about the creasing edge towards the load cell, such that the force exerted on the load cell is in the same rotational direction as the force exerted on the sample.

2. An apparatus as claimed in claim 1 wherein the creasing edge about which the sample is bent remains stationary with respect to the load cell during measurement.

3. A method for determining the crease characteristics of a corrugated paper board sample, said method comprising the steps of:

loading the sample in a sample location area such that a surface of the sample overlies a load cell, and such that a surface opposite the surface which overlies the load cell is adjacent a creasing edge which is laterally spaced from the load cell;

bending the sample about the creasing edge such that the portion of the sample on the side of the creasing edge remote from the load cell is rotated towards the load cell and the force exerted on the load cell is in the same rotational direction as the force exerted on the sample; and measuring the force required to bend the sample with the load cell.

4. A method according to claim 3 further comprising maintaining the creasing edge stationary with respect to the load cell during said measuring step.

5. A method according to claim 3 wherein the step of bending the sample comprises bending the sample manually.

6. A method according to claim 3 comprising the further step of calculating a score test ratio by determining the ratio of the peak folding force of a creased sample to the peak folding force of an uncreased sample.

* * * * *